United States Patent [19]
Brion et al.

[11] Patent Number: 6,136,981
[45] Date of Patent: Oct. 24, 2000

[54] PREPARATION OF 4-PHENYL-1,2,3,6-TETRAHYDROPYRIDINES

[75] Inventors: Francis Brion, Balma; Christian Richard, Rosny sous Bois, both of France

[73] Assignee: Hoechst Marion Roussel, France

[21] Appl. No.: 09/334,776

[22] Filed: Jun. 16, 1999

[30] Foreign Application Priority Data

Jun. 18, 1998 [FR] France ................................. 98 07677

[51] Int. Cl.$^7$ ..................... C07D 211/74; C07D 491/044
[52] U.S. Cl. ........................................... 546/216; 546/113
[58] Field of Search ..................... 546/113, 216

[56] References Cited

U.S. PATENT DOCUMENTS 4,132,710  1/1979  Gauthier et al. ................. 546/63

FOREIGN PATENT DOCUMENTS 979824  2/2000  European Pat. Off. .

(List continued on next page.)

OTHER PUBLICATIONS

Kubela et al. "4–Arylpiperidine derivatives" CA 90:203872, 1977.

(List continued on next page.)

*Primary Examiner*—Ceila Chang
*Attorney, Agent, or Firm*—Bierman, Muserlian and Lucas

[57] ABSTRACT

A process for the preparation of a compound of the formula

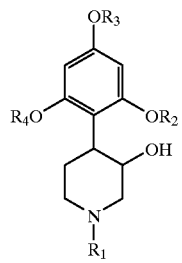

I wherein $R_1$ is selected from the group consisting of hydrogen and alkyl of 1 to 8 carbon atoms, $R_2$ and $R_4$ are alkyl of 1 to 4 carbon atoms and $R_3$ is alkyl of 1 to 8 carbon atoms comprising reacting a compound of the formula

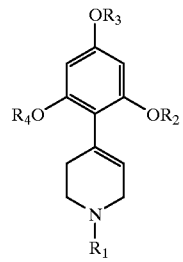

II wherein $R_1$, $R_2$, $R_3$ and $R_4$ are defined as above or an amine salt thereof with an electrophilic halogenating agent to obtain a compound of the formula

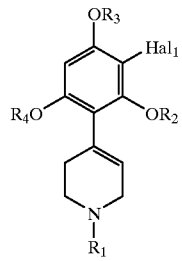

III wherein $Hal_1$ is halogen, reacting the latter with a halohydroxylating agent to obtain a compound of the formula

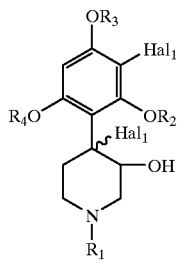

IV wherein $Hal_2$ is halogen, reacting the latter with a base to obtain a compound of the formula

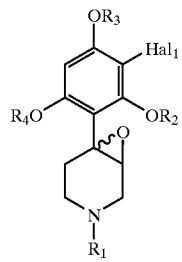

V reacting the latter with a diastereoselective reducing agent to obtain a compound of the formula

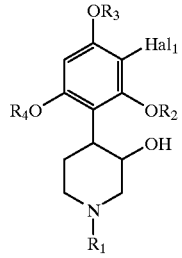

VI reacting the latter with a reducing agent to obtain a cis racemic compound of formula I and optionally resolving the latter with a resolution agent to obtain the desired optical form and novel intermediates.

17 Claims, No Drawings

FOREIGN PATENT DOCUMENTS 2338043    8/1977    France .
9742949    11/1997    WIPO .

OTHER PUBLICATIONS

Ramachandra et al, "An Antiinflammatory . . . Synthesis", Tetrahedraon, vol. 44, No. 7, (1988) pp. 2081–2086.

Nagai et al, "Studies . . . Compounds", Chem. Pharm. Bull., vol. 28, No. 5, (1980) pp. 1387–1393.

Lyle, et al, "Nucleophilic . . . Epoxypiperidine", J. Org. Chem., vol. 32, No. 9, (1967) pp. 2873–2875.

PREPARATION OF 4-PHENYL-1,2,3,6-TETRAHYDROPYRIDINES

OBJECTS OF THE INVENTION

It is an object of the invention to provide an improved process for the preparation of 4-phenyl-1,2,3,6-tetrahydropyridines of formula I and novel intermediates.

These and other objects and advantages of the invention will become obvious from the following detailed description.

THE INVENTION

The novel process of the invention for the preparation of a compound of the formula

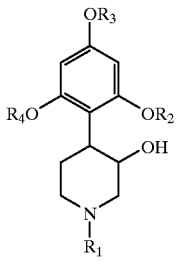

I wherein $R_1$ is selected from the group consisting of hydrogen and alkyl of 1 to 8 carbon atoms, $R_2$ and $R_4$ are alkyl of 1 to 4 carbon atoms and $R_3$ is alkyl of 1 to 8 carbon atoms comprises reacting a compound of the formula

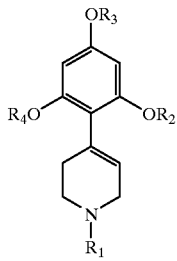

II wherein $R_1$, $R_2$, $R_3$ and $R_4$ are defined as above or an amine salt thereof with an electrophilic halogenating agent to obtain a compound of the formula

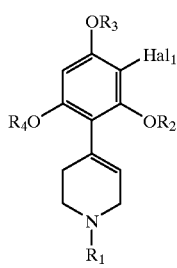

III wherein Hal is halogen, reacting the latter with a halohydroxylating agent to obtain a compound of the formula

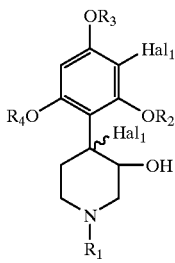

IV wherein $Hal_2$ is halogen, reacting the latter with a base to obtain a compound of the formula

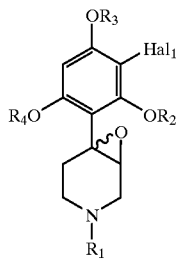

V reacting the latter with a diastereoselective reducing agent to obtain a compound of the formula

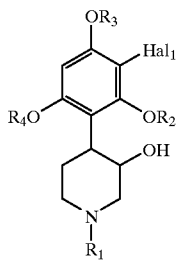

VI reacting the latter with a reducing agent to obtain a cis racemic compound of formula I and optionally resolving the latter with a resolution agent to obtain the desired optical form.

The products of formula I are known products, which can be used particularly for the synthesis of therapeutically active products. The products of formula I, their preparation and their application in the preparation of active products are described in European Patent 0,241,003. The products of formula II used as starting products of the method of the invention are also known products, described in European Patent 0,241,003.

Preferably, $R_1$ is alkyl of 1 to 4 carbon atoms and $R_2$, $R_3$ and $R_4$ are alkyl of 1 to 4 carbon atoms and most preferably, $R_1$, $R_2$, $R_3$ and $R_4$ are all methyl.

In a preferred method of the process, the compound of formula II is used in the form of an amine salt such as its salt with trifluoroacetic acid or hydrobromic acid. Preferably, $Hal_1$ and $Hal_2$ are bromine and the halohydroxylating agent is N-bromo-succinimide and other electrophilic halogenating agents are halogenating or halohydroxylation agents such as N-bromoacetamide and N,N-dibromodimethylhydantoin. The base is preferably sodium hydroxide or potassium hydroxide.

The two intermediates may or may not be isolated. The diastereoselective reducing agent is preferably aluminum hydride (AlH$_3$). The reducing agent for compound VI is preferably zinc in an alcoholic medium or tri-N-butyltin hydride.

Preferably, the products of formulae V, VI and I are resolved using an acid of the formula

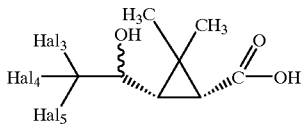

wherein Hal$_3$ is chlorine or bromine or —CF$_3$ and Hal$_4$ and Hal$_5$ are chlorine or bromine. Preferred acids have the formula

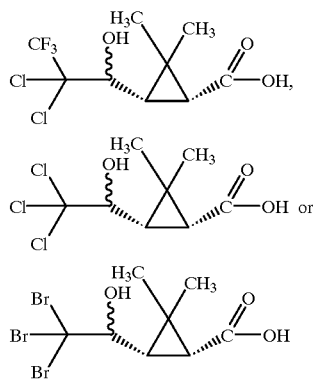

A preferred resolving agent is [1R-(1R*,3S*)]3-(2,2-dichloro-1-hydroxy-3,3,3-trifluoropropyl)-2,2-dimethyl-cyclopropane-carboxylic acid.

The compounds of formulae III, IV, V and VI are novel.

In the following example, there are described several preferred embodiments to illustrate the invention. However, it is to be understood that the invention is not intended to be limited to the specific embodiments.

EXAMPLE

[3S-cis(-)]-1-methyl-4-(2,4,6-trimethoxyphenyl)-3-piperidinol

Step A: 6-(3-bromo-2,4,6-trimethoxyphenyl)-3-methyl-7-oxa-3-aza-bicyclo(4,1,0)heptane.

Salification Stage

A suspension of 100 g of 1-methyl-1,2,3,6-tetrahydro-4-(2,4,6-trimethoxyphenyl)-pyridine and 533 ml of dimethyl-sulfoxide was cooled to 15° C. and over 2 minutes, 133 ml of demineralized water at 20° C. were added. The mixture was cooled to 5°±1° C. and 32 ml of trifluoroacetic acid were added followed by stirring for 15 minutes at 5°±1° C.

Bromination and Hydrobromination Stage 4-(3-bromo-2,4,6-trimethoxyphenyl)-1-methyl-1,2,3,6-tetrahydro-pyridine 4-bromo-4-(3-bromo-2,4,6-trimethoxyphenyl)-1-methyl-3-piperidinol At 5°±1° C., 169 g of N-bromosuccinimide were added to the product of Step A and the mixture was stirred for 90 minutes at 5°±1° C. after which 5 g of sodium metabisulfite were added.

Epoxidation Stage 6-(3-bromo-2,4,6-trimethoxyphenyl)-3-methyl-7-oxa-3-aza-bicyclo(4,1,0)heptane 50 ml of 30% sodium hydroxide were added over about 10 minutes to the preceding solution. The mixture was stirred at 5°±1° C. for 15 minutes and after the addition of 150 ml of 30% sodium hydroxide, the mixture was stirred for 90 minutes.

Isolation

The said suspension was poured into 1000 ml of demineralized water and stirred for 1 hour at 7–10° C. The mixture was filtered and washed with demineralized water and dried to obtain 130.6 g of the desired product.

Step B: cis(±)-1-methyl-4-(2,4,6-trimethoxyphenyl)-3-piperidinol

Preparation of the AlH$_3$/THF Reagent

At about 20° C., 6 g of lithium aluminum hydride were added to 100 ml of THF and the suspension was stirred for 4 hours at 20/25° C. After standing for 20 hours, the mixture was stirred at 0°±1° C. and 5.3 g of anhydrous aluminum chloride were added. The temperature was allowed to rise to 20° C. and the mixture was stirred for 15 minutes at 20° C. to obtain the reducing agent.

Reaction

The suspension above (AlH$_3$/THF) was cooled to 0°±1° C. and at 0°±1° C., a solution of 20 g of product of Step A and 120 ml of THF were added. The mixture was stirred for 2 hours at 0°±1° C. and then 100 ml of a normal solution of sodium hydroxide was added followed by stirring for one hour and the temperature was allowed to rise to about 20° C. The mixture was filtered and the product was washed several times with 20 ml of THF. The filtrate and the wash water were combined and concentrated by distillation at reduced pressure for 1 hour. 300 ml of methanol were added to the solution of cis(±)-4-(3-bromo-2,4,6-trimethoxyphenyl)-1-methyl-3-piperidinol and the mixture was stirred while adding 70 ml of 50% potassium hydroxide. After addition of 20 g of zinc powder, the mixture was refluxed for 16 hours, then cooled to 20° C. The mixture was filtered and washed with 20 ml of anhydrous methanol. The filtrate and the wash waters were concentrated by distillation under reduced pressure. At 20° C., 200 ml of demineralized water were added and the mixture was cooled to 0° C. and stirred for 1 hour at 0° C. The mixture was filtered and washed with 20 ml of water and dried to obtain 13.71 g of the desired product.

Step C: [3S-cis(-)]-1-methyl-4-(2,4,6-trimethoxyphenyl)-3-piperidinol.

A suspension of 12 g of the product of Step B, 12.59 g of [1R-(1R*,3S*)]3-(2,2-dichloro-1-hydroxy-3,3,3-trifluoropropyl)-2,2-dimethyl-cyclopropane-carboxylic acid and 60 ml of ethanol were heated to 70° C. and then at 67° C., 0.12 g of seed crystals in the cis(-) form were added. The reaction mixture was cooled to 25° C. in 5 hours and stirred for 16 hours at 25° C., filtered and rinsed with 12 ml of ethanol. The product was dried at reduced pressure at 50° C. for 16 hours to obtain 9.97 g of the raw product which was recrystallized from methylisobutyl ketone to obtain 7.75 g of the salified required product. 23 ml of demineralized water and 39 ml of isopropyl ether were added thereto and the mixture was stirred at 20° C. The suspension obtained had added thereto 20.1 ml of a 2N hydrochloric acid solution which was decanted. The aqueous phase was washed with 23 ml of isopropyl ether and the acidic phases were combined. 9.7 g of sodium chloride were added and the mixture was stirred and cooled to 0° C. 7.75 ml of sodium hydroxide were added at 30° C. and the mixture was stirred at 0 to -5° C. for 90 minutes. The mixture was filtered and rinsed with demineralized water and the product was dried in an oven at 50° C. for 16 hours to obtain 3.65 g of the desired product melting at 115° C. and having a specific rotation of $[\alpha]_D = -53°3($, $C=2\%$ $CH_3OH)$.

Various modifications of the process of the invention may be made without departing from the spirit or scope thereof and it is to be understood that the invention is intended to be limited only as defined in the appended claims.

What we claim is:

1. A process for the preparation of a compound of the formula

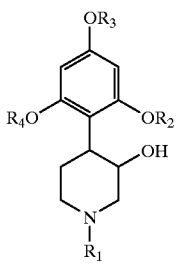

I wherein $R_1$ is selected from the group consisting of hydrogen and alkyl of 1 to 8 carbon atoms, $R_2$ and $R_4$ are alkyl of 1 to 4 carbon atoms and $R_3$ is alkyl of 1 to 8 carbon atoms comprising reacting a compound of the formula

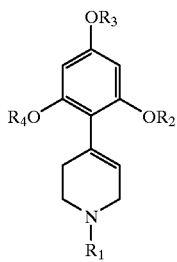

II wherein $R_1$, $R_2$, $R_3$ and $R_4$ are defined as above or an amine salt thereof with an electrophilic halogenating agent to obtain a compound of the formula

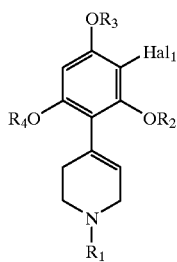

III wherein $Hal_1$ is halogen, reacting the latter with a halohydroxylating agent to obtain a compound of the formula

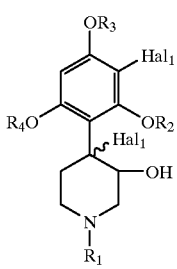

IV wherein $Hal_2$ is halogen, reacting the latter with a base to obtain a compound of the formula

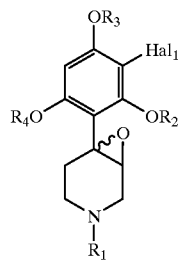

V reacting the latter with a diastereoselective reducing agent to obtain a compound of the formula

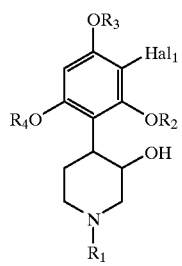

VI reacting the latter with a reducing agent to obtain a cis racemic compound of formula I and optionally resolving the latter with a resolution agent to obtain the desired optical form.

2. The process of claim 1 wherein $R_1$ is alkyl of 1 to 4 carbon atoms.

3. The process of claim 1 wherein $R_2$, $R_3$ and $R_4$ are alkyl of 1 to 4 carbon atoms.

4. The process of claim 1 wherein $R_1$, $R_2$, $R_3$ and $R_4$ are methyl.

5. The process of claim 1 wherein the compound of formula II is in the form of an amine salt.

6. The process of claim 1 wherein $Hal_1$ and $Hal_2$ are bromine.

7. The process of claim 1 wherein the halohydroxylating agent is N-bromosuccinimide.

8. The process of claim 1 wherein the base is sodium hydroxide or potassium hydroxide.

9. The process of claim 1 wherein the diastereoselective reducing agent is aluminum hydride.

10. The process of claim 1 wherein the reducing agent is zinc in an alcoholic medium.

11. The process of claim 1 wherein the resolving agent is an acid of the formula

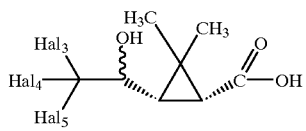

wherein $Hal_3$ is selected from the group consisting of chlorine, bromine and $-CF_3$ and $Hal_4$ and $Hal_5$ are chlorine or bromine.

12. The process of claim 11 wherein the resolving agent has a formula selected from the group consisting of

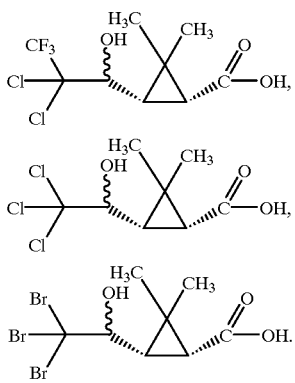

13. The process of claim 11 wherein the resolving agent is [1R-(1R* 3S*)]3-(2,2-dichloro-1-hydroxy-3,3,3-trifluoropropyl)-2,2-dimethylcyclopropane-carboxylic acid.

14. The process of claim 1 wherein the compound of formula II is 1-methyl-1,2,3,6-tetrahydro-4-(2,4,6-trimethoxy-phenyl)-pyridine.

15. A compound of a formula selected from the group consisting of

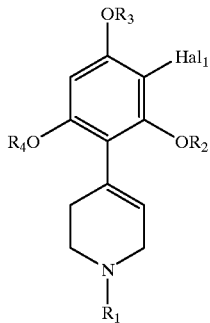

III

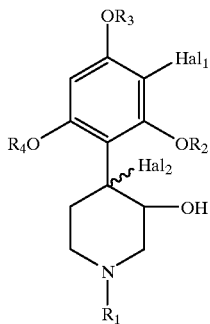

IV

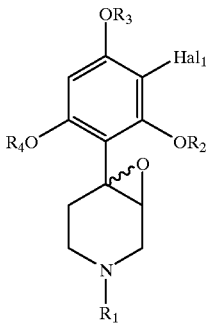

V

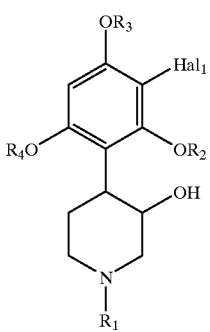

VI wherein $R_1$, $R_2$, $R_3$ and $R_4$ are defined as in claim 1 and $Hal_1$ and $Hal_2$ are halogen.

16. A compound of claim 15 selected from the group consisting of 4-(3-bromo-2,4,6-trimethoxyphenyl)-1-methyl-1,2,3,6-tetrahydropyridine, 4-bromo-4-(3-bromo-2,4,6-trimethoxyphenyl)-1-methyl-3-piperidinol and cis($\pm$)-4-(3-bromo-2,4,6-trimethoxyphenyl)-1-methyl-3-piperidinol.

17. A compound of claim 15 which is 6-(3-bromo-2,4,6-trimethoxyphenyl)-3-methyl-7-oxa-3-azabicyclo(4,1,0)heptane.

* * * * *